US006214815B1

(12) United States Patent
Shangold et al.

(10) Patent No.: US 6,214,815 B1
(45) Date of Patent: Apr. 10, 2001

(54) TRIPHASIC ORAL CONTRACEPTIVE

(75) Inventors: Gary Shangold, Califon, NJ (US);
Arkady Rubin, Brooklyn, NY (US);
David Upmalis, Newtown, PA (US)

(73) Assignee: Ortho-McNeil Pharmaceuticals, Inc.,
Raritan, NJ (US)

( * ) Notice: Subject to any disclaimer, the term of this patent is extended or adjusted under 35 U.S.C. 154(b) by 0 days.

(21) Appl. No.: 09/328,764

(22) Filed: Jun. 9, 1999

Related U.S. Application Data

(60) Provisional application No. 60/113,394, filed on Dec. 23, 1998.

(51) Int. Cl.⁷ .................................................. A61K 31/56

(52) U.S. Cl. ............................................................ 514/170

(58) Field of Search ............................................ 514/170

(56) References Cited

U.S. PATENT DOCUMENTS

| | | | |
|---|---|---|---|
| Re. 35,724 | 2/1998 | Pasquale | 514/170 |
| 3,568,828 | 3/1971 | Lerner | 206/42 |
| 3,836,651 | 9/1974 | Rudel | 424/239 |
| 3,932,635 | 1/1976 | Segre | 424/239 |
| 3,939,264 | 2/1976 | Lachnit-Fixson | 424/239 |
| 3,957,982 | 5/1976 | Lachnit-Fixson | 424/238 |
| 3,969,502 | 7/1976 | Lachnit-Fixson | 424/239 |
| 4,291,028 | 9/1981 | Vorys | 424/238 |
| 4,378,356 | 3/1983 | Jager | 424/238 |
| 4,390,531 | 6/1983 | Edgren | 424/239 |
| 4,530,839 | 7/1985 | Pasquale | 514/171 |
| 4,544,554 | 10/1985 | Pasquale | 514/170 |
| 4,616,006 | 10/1986 | Pasquale | 514/170 |
| 4,628,051 | 12/1986 | Pasquale | 514/170 |
| 4,921,843 | 5/1990 | Pasquale | 514/170 |
| 4,948,593 | 8/1990 | Wright et al. | 424/473 |
| 4,962,098 | 10/1990 | Boissonneault | 514/170 |
| 5,023,084 | 6/1991 | Chien | 424/448 |
| 5,262,408 | 11/1993 | Bergink | 514/182 |
| 5,418,228 | 5/1995 | Bennink | 514/182 |
| 5,453,279 | 9/1995 | Lee et al. | 424/448 |
| 5,585,370 | 12/1996 | Casper | 514/170 |
| 5,747,480 | 5/1998 | Gast | 514/179 |

FOREIGN PATENT DOCUMENTS 0 491 415 A1    5/1991    (EP) ........................... A61K/31/565

OTHER PUBLICATIONS

Schwarz B E Et Al: "Reference period analysis of vaginal bleeding with triphasic oral contraceptive agents containing norethindrone or levonorgestrel: a comparison study." International Journal of Fertility, (1992 May–Jun.) 37 (3) 176–82, XP000881622 pp. 176–177, p. 178; table 1 p. 181.
Lox C D: "Biochemical effects in women following one year's exposure to a new triphasic contraceptive–I. Chemistry profiles." General Pharmacology, (Mar. 1996 27 (2) 367–70., XP000881634 p. 367.

A twelve–month Comparative Clinical Investigation of Two Low–Dose Oral Contraceptives Containing 20 ug Ethinylestradiol/75 ug Gestodene and 30 ug Ethinylestradiol/75 ug Gestodene With Respect to Efficacy, Cycle Control, and Tolerance, Endrilkat, J., U. Muller, and B. Dusterberg, Contaception 1977; 55: 131–137.
Investigation of the Influence of Two Low–dose Monophasic Oral Contraceptives Containing 20 ug Ethinylestradiol/ 75 ug Gestodene and 30 ug Ethinylestradiol/75 ug on Lipid Metabolism in an Open Randomized Trial, Brill, K., A. Then, U Beisiegel, A. Jene, C. Wunsch, and F. Leidenberger, Contraception 1996; 54: 291–291.
A Clinical Comparison in Finland of Two Oral Contraceptives containing 0.150 mg Desogestrel in Combination with 0.020 mg or 0.030 mg Ethinylestradiol, Acta Obstet Gynecol Scand Suppl 1987; 144: 7–12, Tuimala, R., M. Saranen, and U. Alapiessa.
Oral Contraceptive Tablets Containing 20 and 30 Ug of Ethinyl Estradiol with 150 ug Desogestrel, Aceta Obstet Gynecol Scand 1994; 73: 136–143, Akerlund, M., E. Almstrom, S.Hogsted, and M. Nabrink.
Comparative Profiles of Reliability, Cycle Control, and Side Effects of Two Oral Contraceptive Formulations Containing 150 ug Desogestrel and Either 30 ug or 20 ug Ethinyl Estradiol, British Journal of Obstetrics and Gynaecology Sep. 1993, vol. 100, pp. 832–838, Akerlund, M., A. Rode, and J. Westergaard.
Dialogues in Contraception, vol. 5, No. 5, "Contraception— Associated Menstrual Problems: Etiology and Management," Spring 1998, Darney, P.D. et al., pp. 1–11.
Hemostatic and Metabolic Effects of Lowering the Ethinyl Estradiol Dose From 30 mcg to 20 mcg in Oral Contraceptives Containing Desogestrel, Contraception 1993: 48, Sep., Basdevant, A, J. Contrad, C. Pelissier, et al.
A Randomized Double–Blind Study of Six Combined Oral Contraceptives, Contraception 1982 Vol. 25, No. 3, Task Force on Oral Contraceptives–WHO Special Program of Research, Development, and Research Training in Human Reproduction, pp. 231–241.

(List continued on next page.)

*Primary Examiner*—Russell Travers
(74) *Attorney, Agent, or Firm*—John Harbour

(57) ABSTRACT

A method of contraception in which an estrogen and a progestogen are administered daily in a three phase sequence for 21 days is disclosed. In the first phase a combination of an estrogen and a progestogen in a low but contraceptively effective daily dosage corresponding in estrogenic activity to 23–28 µg of 17α-ethinylestradiol and in progestogenic activity to 0.065–0.75 mg of norethindrone is administered for 5–8 days; followed by the administering of the same dosage of estrogen and a progestogen corresponding in progestogenic activity to 0.25–1.0 mg of norethindrone for 7–11 days; followed by the administering of the same dosage of estrogen and a progestogen corresponding in progestogenic activity to 0.35–2.0 mg of norethindrone for 3–7 days; followed by 4–8 days without administering either an estrogen or a progestogen.

4 Claims, No Drawings

OTHER PUBLICATIONS

The effect of oestrogen dose and progestogen type on haemostatic changes in women taking low dose oral contraceptivs, British Journal of Obstetrics and Gynaecology, Mar. 1996, vol. 103, pp. 261–267, L. A. Norris, J. Bonnar.

Effect of Oral Contraceptives Containing 20 and 35 ug Ethinyl Estradiol on Urinary Prostacyclin and Thromboxane Levels in Smokers and Non–Smokers, Susan Pioszal, MD, Melvin H. Thornton MD, Frank Z. Stanczyk PhD, Daniel R. Mishell, Jr., MD, Dept of Ob/Gyn, University of Southern California School of Medicine, Los Angeles, CA (1998), P. 60.

Changes in Androgens During Treatment with Four Low–Dose Contraceptives, C.M.H. Coenen, C.M.G. Thomas, G.F. Borm, J.M.G. Hollanders, and R. Rolland, Contraception 1996; 53: 171–176.

TRIPHASIC ORAL CONTRACEPTIVE

This application claims benefit of Provisional Application 06/113,394, Dec. 23, 1998.

The present invention relates to triphasic oral contraceptive regimens of steroids. More particularly, the present invention relates to a triphasic contraceptive regimen containing a progestin and low doses of ethinyl estradiol (EE).

BACKGROUND OF THE INVENTION a) Low Dose Estrogen Regimens

In the past years, it has been recognized that there are certain benefits associated with steroid based oral contraceptives, i.e. OCs, having lower doses of progestin, and especially, lower doses of estrogen. Such benefits of lower estrogen doses include decreased incidence of nuisance side effects, such as, nausea, vomiting, and gastric upset, as well as a decreased incidence of serious side effects, such as, thromboembolism, stroke, and myocardial infarction. Thus, while the advantages of steroid based contraceptives are well established in the medical community, it is desirable to administer the lowest effective dose of steroids, on a patient by patient basis, in order to minimize these types of side effects.

A principle problem with lower doses of estrogen in an OC regimen is poor cycle control and the patient compliance problems associated with poor cycle control. At estrogen doses below 30 μg per day, it has been observed that the incidence of breakthrough bleeding and/or spotting is increased to the point that many women can be expected to experience additional discomfort due to irregular bleeding. This failure to control the cycle will lead many women to unnecessarily return to higher estrogen doses, stop using contraception or fall out of compliance with the prescribed regimen. It is well recognized that the symptoms of poor cycle control influence the occurrence of unintended pregnancies by encouraging the cessation of OC use by women who do not wish to become pregnant.

Endrikat, J.; U. Muller, and B. Dusterberg; *Contraception* 1997; 55: 131–137 compared a 20 μg and 30 μg ethinyl estradiol (EE) monophasic regimen for cycle control. In this regimen, women received either tablets containing 20 μg of EE and 75 μg gestodene or 30 μg of EE and 75 μg of gestodene. The regimen was a monophasic 21 days of active tablets followed by a tablet-free period of 7 days. A higher incidence of breakthrough bleeding and/or spotting was apparent for the 20 μg EE regimen. The breakthrough bleeding and/or spotting results disclosed by this article are more fully summarized below as COMPARATIVE EXAMPLE A.

Tuimala, R.; M. Saranen; and U. Alapiessa; *Acta Obstet Gynecol Scand* 1994; 144: 7–12 compared a 20 μg and 30 μg ethinyl estradiol (EE) monophasic regimen for cycle control. In this regimen, women received either tablets containing 20 μg of EE and 150 μg desogestrel or 30 μg of EE and 150 μg desogestrel. The regimen was a monophasic 21 days of active followed by a tablet-free period of 7 days. A higher incidence of breakthrough bleeding and/or spotting was apparent for the 20 μg EE regimen. The breakthrough bleeding and/or spotting results disclosed by this article are more fully summarized below as COMPARATIVE EXAMPLE B.

Akerlund, M.; A. Rode; and J. Westergaard; *Brit J Obstet Gynecol* September 1993; 100: 832–838 compared a 20 μg and 30 μg ethinyl estradiol (EE) monophasic regimen for cycle control. In this regimen, women received either tablets containing 20 μg of 15 EE and 150 μg desogestrel or 30 μg of EE and 150 μg desogestrel. The regimen was a monophasic 21 days of active followed by a tablet-free period of 7 days. A higher incidence of breakthrough bleeding and/or spotting was apparent for the 20 μg EE regimen. The breakthrough bleeding and/or spotting results disclosed by this article are more fully summarized below as COMPARATIVE EXAMPLE C.

Darney, P.; and C. Klaisle; *Dialogues in Contraception*; Vol. 5, Number 5, Univ. of Southern California School of Medicine, survey various literature sources and conclude that OCs containing 20 μg estrogen, such as a monophasic regimen containing 20 μg EE and 100 μg levonorgestrel, have higher rates of breakthrough bleeding and spotting than do formulations containing 30 or 35 μg estrogen.

Task Force on Oral Contraceptives—WHO Special Program of Research, Development, and Research Training in Human Reproduction; *Contraception* 1982; Vol. 25, Number 3, demonstrates that a combination of 1 mg norethindrone acetate and 50 μg of EE has better cycle control than a combination of 1 mg norethindrone acetate and 20 μg of EE.

Thus, there exists a need for an OC containing an estrogen dose of less than 30 μg per day yet having cycle control equivalent to an OC of higher estrogen content.

b) Triphasic Regimens

Three-stage or triphasic combination type oral contraceptive regimens are known. Triphasic regimens of various types are described in U.S. Pat. Nos. 4,390,531; 4,066,757; 3,957,982; 3,795,734; and 2,431,704.

More recently, Pasquale S., U.S. Pat. Nos. 4,530,839; 4,544,554; 4,616,006; and 4,628,051 described a triphasic regimen of contraception which comprises administering for 21 successive days to a female of childbearing age a combination of an estrogen and a progestogen in a low but contraceptively effective daily dosage corresponding in estrogenic activity to 20–50 μg of 17α-ethinylestradiol and in progestogenic activity to 0.065–0.75 mg of norethindrone for 5–8 days; for the next 7–11 days an estrogen daily dosage equal to 20–50 μg of 17α-ethinylestradiol and in progestogenic activity to 0.250–1.0 mg of norethindrone; and for the next 3–7 days an estrogen daily dosage equal to 20–50 μg of 17α-ethinylestradiol and in progestogenic activity 0.35–2.0 mg of norethindrone; followed by 6–8 days without estrogen and progestogen administration, provided that the estrogen daily dosage is the same for each period. The purpose of this regimen is to lower the total monthly steroid dose in the oral contraceptive while still obtaining equivalent bleeding patterns and protection against pregnancy as found with conventional oral contraceptives.

Particular triphasic regimens of Pasquale have met with considerable commercial success. One commercial regimen with norgestimate has been marketed by Ortho-McNeil Pharmaceutical Inc. in the United States under the trademark ORTHO TRI-CYCLEN. According to this regimen, there is administered 7 days of a tablet containing 35 μg 17α-ethinylestradiol and 0.180 mg norgestimate, followed by 7 days of a tablet containing 35 μg 17α-ethinylestradiol and 0.215 mg norgestimate, followed by 7 days of a tablet containing 35 μg 17α-ethinylestradiol and 0.250 mg norgestimate, followed by 7 days of a placebo. Another commercial regimen with norethindrone has been marketed by Ortho-McNeil Pharmaceutical Inc. in the United States under the trademark ORTHO-NOVUM 7/7/7. According to this regimen, there is administered 7 days of a tablet containing 35 μg 17α-ethinylestradiol and 0.5 mg norethindrone, followed by 7 days of a tablet containing 35 μg 17α-ethinylestradiol and 0.75 mg norethindrone, followed by 7 days of a tablet containing 35 μg 17α- ethinylestradiol and 1.0 mg norethindrone, followed by 7 days of a placebo. These regimens have proven particularly successful at controlling the cycle of women as well as protecting against pregnancy at relatively low total monthly steroid doses.

There is a need, however, for a combination type contraceptive which contains even lower total monthly steroid doses, particularly of estrogen, yet is still effective for the prevention of pregnancy and maintains a high level of cycle control.

There remains a need for a triphasic regimen of contraception with substantially lower doses of estrogen, yet does not exhibit a substantial loss of cycle control.

SUMMARY OF THE INVENTION

According to the present invention, a method of reliable contraception is achieved at low doses of estrogen by administering for a total of 20 to 24 successive days to a female of child bearing age a combination of an estrogen and a progestogen in a contraceptively effective daily dosage in which there is a first phase of 5–8 days where the combination comprises a progestogen equivalent in effect to about 0.065–0.75 mg of norethindrone and an estrogen equivalent in effect to about 23–28 µg of ethinyl estradiol; followed by a second phase of 7–11 days, where the combination comprises a progestogen equivalent in effect to about 0.25–1.0 mg of a norethindrone and an estrogen equivalent in effect to about 23–28 µg of ethinyl estradiol; followed by a third phase of 3–7 days where the combination comprises a progestogen equivalent in effect to about 0.35–2.0 mg of norethindrone in combination with an estrogen equivalent in effect to about 23–28 µg of ethinyl estradiol; and followed by 4–8 days which are free of hormone administration; with the provisos that the progestin dose should increase from the first phase to the second phase to the third phase and that the dosage of estrogen is kept constant in each phase. The actual weight amount of the dosage at each dosage level will depend upon the estrogenic and progestogenic activity, respectively, of the components selected for the dosage units.

Applicants have surprisingly discovered for this triphasic regimen and as demonstrated below, that the reduced level of estrogen administration does not result in a commensurate reduction in cycle control.

DETAILED DESCRIPTION OF THE INVENTION

The total number of days during which the progestogen and estrogen combinations are administered daily is preferably 21. These are followed by 4–8 days which are free of hormone administration to approximate the natural 28-day menstrual cycle of the female. Day one of the cycle is defined as the first day of menstruation and the days are numbered sequentially thereafter until menstruation occurs again. The cycle usually lasts 28 days but it may be slightly longer or shorter. In actual practice, the placebo or any of the hormone containing tablets might contain nutritional supplements such as, for example, iron supplements, folic acid, calcium, etc. Thus, in a preferred regimen, phase one would commence sometime between day 1 and day 7 of the menstrual cycle and last 5–8 days but preferably 7 days, phase two would last 7–11 days, preferably 7 days, while phase three would last 3 to 7 days, preferably 7 days.

The contraceptive composition employed in the present invention comprises separate daily dosage units which are adapted for successive daily oral ingestion. The composition consists essentially of, as the first phase, 5–8 dosage units containing, in admixture with a pharmaceutically acceptable carrier, a combination of an estrogen in combination with a progestogen, followed by, as the second phase, 7–11 dosage units containing, a combination of estrogen and a progestogen, followed by, as the third phase, 3–7 dosage units containing a combination of an estrogen and a progestogen optionally followed by 48 dosage units free of estrogen and progestogen. The estrogen daily dosage is kept constant in all three phases.

Any conventional estrogen may be employed as a suitable component in the contraceptive regimen of this invention. The particular regimen employed in a daily dosage should be equal in contraceptive activity in each phase to a daily dosage of about 23–28 µg of 17α-ethinylestradiol. The preferred dosage is one equal to a daily dosage of about 25 µg of 17α-ethinylestradiol.

In addition to 17α-ethinylestradiol, esters and ethers of 17α-ethinylestradiol such as, for example, 17α-ethinylestradiol 3-dimethylamino propionate, 17α-ethinylestradiol 3-cyclopentyl ether (quienestrol) and 17α-ethinylestradiol 3-methyl ether (mestranol) may also be employed as the estrogen component. Natural estrogens such as estrone, estrone sulfate, estrone sulfate piperazine salt, estradiol and estriol, and their esters, as well as the synthetic estrogens, may also be employed. The preferred estrogen is 17α-ethinylestradiol or 17α-ethinylestradiol 3-methyl ether.

As the progestogen component, any progestationally active compound may be employed. The progestogen is preferably administered in a daily dosage in the first phase corresponding in progestogenic activity to 0.065–0.75 mg of norethindrone per day, during the second phase a daily dosage corresponding in progestogenic activity to 0.25–1.0 mg of norethindrone per day and during the third phase a daily dosage corresponding in progestogenic activity to 0.35–2.0 mg of norethindrone per day. It is an aspect of the present invention that the progestin dose should substantially increase from the first phase to the second phase to the third phase. The progestogen is more preferably administered in a daily dosage in the first phase corresponding in progestogenic activity to 0.25–0.65 mg of norethindrone per day and most preferably 0.40–0.60 mg of norethindrone per day, during the second phase a daily dosage corresponding in progestogenic activity to 0.35–0.9 mg of norethindrone per day and most preferably 0.65–0.85 mg norethindrone per day, and during the third phase a daily dosage corresponding in progestogenic activity to 0.50–1.50 mg of norethindrone per day and most preferably 0.9–1.1 mg norethindrone per day. An example dose of norethindrone is in the first phase is 0.50 mg, in the second phase is 0.75 mg and in the third phase is 1.0 mg.

Progestogens which may be employed as a component in the present invention include progesterone and its derivatives such as, for example, 17-hydroxyprogesterone esters and 19-nor-17-hydroxyprogesterone esters, 17α-ethinyltestosterone, 17α-ethinyl-19-nortestosterone and derivatives thereof, norethindrone, D-norgestrel, $\Delta^{15}$ levonorgestrel, $\Delta^{15}$ levonorgestrel acetate, $\Delta^{15}$ levonorgestrel acetate oxime, D-17β-acetoxy-β-ethyl-17α-ethinyl-gon-4-en-3-one oxime (norgestimate), desogestrel, ethynodiol diacetate, dydrogesterone, medroxyprogesterone acetate, norethynodrel, allylestrenol, lynoestrenol, quingestranol acetate, medrogestone, norgestrienone, dimethisterone, ethisterone, cyproterone acetate, chlormadinone acetate, and magestrol acetate. Preferred progestogens are norethindrone and norgestimate.

Corresponding progestogenic activity between progestogens in general and norethindrone in particular is well reported in the literature. Table 1 below is taken from the literature and is reported herein for convenience.

TABLE 1

| Progestogen | Preferred Dosage (mg/day) | Dosage Range (mg/day) |
|---|---|---|
| Norethindrone | 0.75 | 0.065–2.0 |
| Norgestimate | 0.22 | 0.03–0.90 |
| D-Norgestrel | 0.1 | 0.05–0.15 |
| $\Delta^{15}$ levonorgestrel | 0.05 | 0.025–0.075 |
| Desogestrel | 0.15 | 0.05–1.0 |
| Ethynodiol diacetate | 0.30 | 0.1–1.0 |
| Dydrogesterone | 10 | 5–30 |
| Medroxyprogesterone acetate | 2.5 | 1–15 |
| Norethynodrel | 1 | 0.2–5.0 |
| Allylestrenol | 2 | 1–10 |
| Lynoestrenol | 0.2 | 0.1–2.0 |
| Quingestranol acetate | 0.2 | 0.05–1.0 |
| Medrogestone | 2 | 1–10 |
| Norgestrienone | 0.05 | 0.02–0.2 |
| Dimethisterone | 1 | 0.5–15 |
| Ethisterone | 2.5 | 1–25 |
| Cyproterone acetate | 0.5 | 0.1–10 |
| Chlormadinone acetate | 0.3 | 0.1–1.0 |
| Magestrol acetate | 1.0 | 0.1–10 |

Where the progestogen is norgestimate, it is preferably administered in a daily dosage in the first phase of 0.03–0.25 mg per day, during the second phase a daily dosage of 0.1–0.35 mg per day and during the third phase a daily dosage of 0.15–0.50 mg per day. Norgestimate is more preferably administered in a daily dosage in the first phase of 0.1–0.22 mg per day and most preferably 0.15–0.20 mg per day, during the second phase a preferred daily dosage of 0.15–0.30 mg per day and most preferably 0.2–0.23 mg per day, and during the third phase a daily dosage of 0.20–0.40 mg per day and most preferably 0.23–0.3 mg per day. A example dose of norgestimate in the first phase is 0.180 mg, in the second phase is 0.215 mg and in the third phase is 0.250 mg.

The estrogen and progestogen components are preferably administered together orally in a pharmaceutically acceptable nontoxic carrier, but they can also be administered separately or parenterally. In general, the effective agents are processed, together with the usually additives, vehicles and/or flavor-ameliorating agents normally employed in Galenic pharmacy, in accordance with generally accepted pharmaceutical practices. For the preferred oral administration, tablets, dragees, capsules, pills, suspensions or solutions are particularly suitable; for parenteral application, oily solutions such as, for example, sesame oil or castor oil solutions which can optionally additionally contain a diluent such as, for example, benzyl benzoate or benzyl alcohol.

In the case of the preferred oral application, the three-phase combination-type contraceptives are preferably packaged in the form of a pharmaceutical kit or package in which the daily dosages are arranged for proper sequential administration. This invention also relates, therefore, to a pharmaceutical unit which contains combination-type contraceptives in dosage units in a synchronized, fixed sequence, wherein the sequence or arrangement of the dosage units corresponds to the stages of daily administration.

The pharmaceutical unit can be, e.g., in the form of a transparent package having dosage units arranged sequentially and consisting of the tablets for the first phase, followed by the tablets for the second phase, followed by the tablets for the third phase, and finally optionally followed by the placebos. A single tablet is to be taken each day over the period of the cycle.

Without further elaboration it is believed that one skilled in the art, using the preceding description, can fully utilize the present invention. The following preferred specific embodiments are to be construed as merely illustrative of the invention and are not meant to limit the invention in any way.

COMPARATIVE EXAMPLE A

SUBJECTS AND METHODS

This double-blind, randomized, comparative study was carried out in 10 centers in Germany over a period of 12 cycles as fully described by Endrikat, J.; U. Muller; and B. Dusterberg; *Contraception* 1997; 55: 131–137. The following is reported here for convenience and is incomplete as compared to the fill text of the article.

A total of 649 healthy, sexually active women between 18 and 39 years of age, who required contraception for at least 12 months, were recruited for the study. The volunteers included both new users and women switching from another oral contraceptive. Women were excluded from the study if they had used parenteral depot-contraceptives during the last six months, had liver disease, vascular or metabolic diseases, tumors, pregnancy, diagnostically unclassified genital bleeding, and all other known contraindications for OC use. A desire for contraception over at least 12 months was essential. Women received strips of pills containing either 21 sugar-coated tables of the test preparation, which contained 20 µg EE and 75 µg GSD (SH D 543 A, Schering AG), or the reference preparation, which contained 21 tablets of 30 µg EE and 75 µg GSD (FEMODENE, SH D 356 C, Schering AG). Women started taking the study preparations on the first day of their next menstrual period.

Comments regarding cycle control and adverse events were documented by the subjects on their menstruation chart. Intermenstrual bleeding was classified as either spotting (scanty bleeding), which required no sanitary protection, or breakthrough bleeding (normal/excessive bleeding), which required sanitary protection.

RESULTS

In all, 428 cases with a total of 4470 cycles of treatment were evaluated for the oral contraceptive containing 20 µg EE and 75 µg GSD (SH D 543 A—test preparation, 20 µg EE preparation) and 221 cases with a total of 2377 cycles were evaluated for the oral contraceptive containing 30 µg EE and 75 µg GSD (SH D 356 C—reference, 30 µg EE preparation). A maximum of 12 cycles was included in all data analyses. A total of 74.6% of the subjects treated with the 20 µg EE preparation and 76.6% of the women under the 30 µg EE preparation completed 12 cycles of treatment. About 95% of the volunteers did not miss any pill during the study. A total of 5.1 % of women taking the 20 µg EE preparation and 4.9% of the women taking the reference preparation (30 µg EE) missed one or more pills in the course of the study.

During the course of the study, 161 volunteers withdrew for various reasons. In total, 93 women (21.7%) in the 20 µg EE group and 40 (18.0%) in the 30 µg EE group were discontinued by the volunteer or by the physician. Sixteen women (3.7%) (20 µg EE) and 12 women (5.4%) (30 µg EE) were excluded by the sponsor. In these cases the study was terminated because of protocol violations or (in some cases) volunteers had not completed all the treatment cycles at the time of the planned evaluation of the study.

Compliance during the study was generally good, and similar in the two groups. When pill-intake was analyzed by cycle, it was found that between 92.9% and 96.9% of women in the 20 µg EE group did not miss any pills. The corresponding figures for the 30 µg EE group ranged from 92.6% to 97.7% in any given cycle.

The frequency of any intermenstrual bleeding (spotting as well as normal or excessive breakthrough bleeding) generally decreased under both preparations from the first three cycles to cycle 12 (Table 2). The highest incidence of spotting (spotting only) was reported by 22.6% of the subjects under the 20 µg preparation (SH D 543 A) and by 13.8% of the subjects under the 30 µg EE oral contraceptive (FEMONDENE) in the first cycle (Table 2). The highest incidence of normal/excessive breakthrough bleeding (breakthrough bleeding only) was reported by 2.4% in the third 20 µg EE cycle. Thereafter, the number of women with any type of intermenstrual bleeding declined continuously to low levels of less than 7% and 5%, respectively. The majority of women had fewer than two treatment cycles with breakthrough bleeding. The values reported in Table 2 were obtained by reading or estimating the value from bar charts in the original article.

TABLE 2

| Cycle | Breakthrough Bleeding (% of subjects) | | Spotting (Only) (% of subjects) | |
| --- | --- | --- | --- | --- |
| | 20 µg EE | 30 µg EE | 20 µg EE | 30 µg EE |
| 0 | 6 | 5 | 4 | 3 |
| 1 | 28 | 18 | 23 | 14 |
| 2 | 17 | 15 | 13 | 11 |
| 3 | 16 | 11 | 11 | 8 |
| 4 | 15 | 9 | 10 | 6 |
| 5 | 14 | 5 | 11 | 4 |
| 6 | 14 | 11 | 11 | 9 |
| 7 | 12 | 6 | 10 | 5 |
| 8 | 13 | 4 | 10 | 4 |
| 9 | 10 | 7 | 7 | 6 |
| 10 | 11 | 5 | 8 | 5 |
| 11 | 7 | 6 | 7 | 5 |
| 12 | 8 | 5 | 5 | 4 |

A total of 47.4% of all women taking the 20 µg EE preparation reported spotting at least once during treatment, but not in every cycle. The corresponding figure for the 30 µg EE preparation was 35.5%. These rates were compared by means of the Fisher Test and were found to be significantly different (p<0.05). The corresponding breakthrough bleeding rates of 14.5% and 11.8% of the women were not statistically different (p>0.05).

COMPARATIVE EXAMPLE B

SUBJECTS AND METHODS

This study compared the results of two separately performed open multicenter trials in a total of 270 women who were recruited in 20 outpatient clinics in different parts of Finland by either general practitioners or gynecologists. The results are fully described by Tuimala, R.; M. Saranen; and U. Alapiessa; *Acta Obstet Gynecol Scand* 1994; 144: 7–12. The following is reported here for convenience and is incomplete as compared to the full text of the article.

Only women of fertile age, with regular cycle control and normally exposed to risk of pregnancy were admitted to the trials. Women who had used other contraceptives before, should have terminated their previous treatment at least 2 months before the start of the investigation and should have experienced at least two spontaneous menstrual periods. Women with any generally accepted contraindication for oral contraceptive use were excluded.

Of the 270 women who participated in the two trials, 91 used the oral contraceptive combination 0.150 mg desogestrel +30 µg ethinylestradiol Marvelon®) for a total of 964 (treatment) cycles in one trial, while the other 179 women used the combination 0.150 mg desogestrel +20 µg ethinylestradiol (Mercilon®) for a total of 2096 cycles in the other trial. Since the two trials were set up as separate studies, there was no randomization in the assignment of women to the two treatment groups. Both treatments are monophasic. Each treatment cycle consists of a period of 21 days of daily tablet intake (1 tablet per day) followed by a tablet-free period of 7 days.

RESULTS

Efficacy of both the 0.150/0.030 and the 0.150/0.020 mg desogestrel/EE combination was good. There were no pregnancies with either contraceptive combinations.

As reported, both preparations showed a good control of irregular bleeding (Table 3). With both preparations the frequency or absence of irregular bleeding increased from almost 80% in cycle one to approximately 85–90% in the subsequent treatment cycles. In general, fewer than 5% of the women experienced an unacceptable irregular bleeding with either preparation.

TABLE 3

| Cycle | Breakthrough Bleeding (% of subjects) | | Spotting (Only) (% of subjects) | |
| --- | --- | --- | --- | --- |
| | 20 µg EE | 30 µg EE | 20 µg EE | 30 µg EE |
| 1 | 9.5 | 7.7 | 13.9 | 13.2 |
| 3 | 5.4 | 5.1 | 10.7 | 5.1 |
| 6 | 2.8 | 5.6 | 7.7 | 9.9 |
| 12 | 7.1 | 0.0 | 9.5 | 7.5 |

COMPARATIVE EXAMPLE C

SUBJECTS AND METHODS

Oral contraceptives containing 0.150 mg desogestrel and 20 or 30 µg of EE per tablet (Mercilon® and Marvelon®/Desolett®, respectively) were compared in 1000 women over a treatment period of one year as fully described by Akerlund, M.; A. Rode; and J. Westergaard; *Brit J Obstet Gynecol* September 1993; 100: 832–838. The sample size of the study (2×500 participants) was determined so that it would be possible to demonstrate that there was a minimal difference with respect to presence of irregular bleeding. The following is reported here for convenience and is incomplete as compared to the full text of the article.

Women asking for oral contraception were recruited for the study. In Norway 300 women were recruited for the study (six centres, all private gynaecological practics), in Sweden 500 women (two university clinics, two central hospitals, one private practice) and in Denmark 200 women (one university clinic). The participating women were aged 18 to 35 (Norway) or 18 to 40 years (Sweden, Denmark). The women were randomly allocated to the study medication according to a list provided by Organon International bv (Oss, The Netherlands): 485 women on the 150/20 µg and 497 on the 150/30 µg combination. The tablets were supplied by Organon International bv in standard, unmarked 21 day blister packs. Women either changed from another OC formulation to the study medication (switchers) or had not used any hormonal contraceptive medication for at least two months (starters).

The women started to take the study medication on the first day of menstruation or of withdrawal bleeding after previous OC pill use. The tablets were taken for 21 consecutive days followed by a seven-day, tablet-free period. Follow up visits were done after three, six and 12 months of OC-treatment with recording of blood pressure and body weight. Furthermore, throughout the study the women noted all vaginal bleeding on specifically designed diary cards, on which each tablet intake and all side effects also were recorded. Completed diary cards were collected, and new cards, as well as new study medication, were distributed at follow up visits. At the final visit gynaecological examination was again performed and haemoglobin concentration measured.

Bleeding was defined as normal withdrawal bleeding if it started within the tablet-free interval and lasted no more than eight days. Any other bleeding during the tablet-taking period was defined as irregular bleeding. Bleeding was further subdivided into spotting (requiring at the most one sanitary pad or tampon a day) or breakthrough bleeding (requiring more than one sanitary pad or tampon a day). The occurrence and duration of these two types of bleeding irregularities were calculated. Days of break through bleeding and spotting within the same bleeding episode were all counted as breakthrough bleeding.

Data on 4543 cycles with the 150/20 $\mu$g and 4688 cycles with the 150/30 $\mu$g combination were obtained. The decrease in number of subjects from start of the study to cycle 1 was due to women electing to participate and receiving a study drug, but thereafter not commencing the medication.

RESULTS

After the study was completed, 8900 cycles were available as recorded on the diary cards. After data validation 8573 cycles could be included in the analysis. The occurrence of irregular bleeding (breakthrough bleeding or spotting) is shown in (Table 4) for all the study cycles. Irregular bleeding was more frequent with the lower EE dose pill than with the higher one. The difference was statistically significant in two-thirds of the cycles randomly distributed over the one year of the study. The incidence of spotting and breakthrough bleeding decreased with increasing duration of use of both OCs. A similar trend was seen in a subanalysis of those women who completed the study. However, the first six months of the study period showed a lower incidence of irregular bleeding in this group compared with the total study population due to the women having dropped out of the study. The values reported in Table 4 were obtained by reading or estimating the value from bar charts in the original article.

TABLE 4

| | Breakthrough Bleeding (% of subjects) | | Spotting (Only) (% of subjects) | | Total BTB and/or Spotting (% of subjects) | |
|---|---|---|---|---|---|---|
| Cycle | 20 $\mu$g EE | 30 $\mu$g EE | 20 $\mu$g EE | 30 $\mu$g EE | 20 $\mu$g EE | 30 $\mu$g EE |
| 1 | 11 | 10 | 25 | 18 | 36 | 28 |
| 2 | 12 | 4 | 13 | 12 | 25 | 16 |
| 3 | 13 | 7 | 12 | 11 | 25 | 18 |
| 4 | 10 | 8 | 11 | 7 | 21 | 15 |

TABLE 4-continued

| | Breakthrough Bleeding (% of subjects) | | Spotting (Only) (% of subjects) | | Total BTB and/or Spotting (% of subjects) | |
|---|---|---|---|---|---|---|
| Cycle | 20 $\mu$g EE | 30 $\mu$g EE | 20 $\mu$g EE | 30 $\mu$g EE | 20 $\mu$g EE | 30 $\mu$g EE |
| 5 | 8 | 7 | 13 | 6 | 21 | 13 |
| 6 | 10 | 6 | 8 | 6 | 18 | 12 |
| 7 | 9 | 6 | 10 | 5 | 19 | 11 |
| 8 | 7 | 5 | 13 | 6 | 20 | 11 |
| 9 | 7 | 5 | 10 | 6 | 17 | 11 |
| 10 | 5 | 4 | 12 | 6 | 17 | 10 |
| 11 | 6 | 4 | 9 | 7 | 15 | 11 |
| 12 | 4 | 3 | 10 | 4 | 14 | 7 |

EXAMPLE 1

SUBJECTS AND METHODS

There was conducted a randomized, multi-center study to evaluate three blinded regimens of norgestimate and ethinyl estradiol (NGM/EE) oral contraceptive and an open-label control regimen. One of these blinded regimens was a triphasic regimen embodying the present invention. In this triphasic regimen there was administered in the first phase a tablet containing 0.180 mg of norgestimate +25 $\mu$g EE once a day for 7 days; in the second phase a tablet containing 0.215 mg of norgestimate +25 $\mu$g EE once a day for 7 days; and in the third phase a tablet containing 0.250 mg of norgestimate +25 $\mu$g EE; followed by 7 days of placebo tablets. Approximately 6300 subjects were enrolled in the full study. The ratio of subjects assigned to each of the three blinded regimen groups versus the open label control regimen group was 3:2. The first 500 subjects in each of the three blinded regimen groups were expected to complete 13 cycles. All other subjects were enrolled for 6 cycles. An Interactive Voice Randomization System (IVRS) was used to randomize subjects into the study.

Subjects who satisfied the following inclusion criteria and did not meet any of the exclusion criteria were admitted to the study.

Inclusion Criteria:
  are 18 to 45 years old. Women between the ages of 35 and 45 must be nonsmokers.
  are sexually active with regular coitus.
  have regular menses occurring every 25–35 days.
  are within the acceptable body mass index.
  have had at least two normal menstrual periods (typical in duration and amount of flow for that subject) which occurred after her last pregnancy.
  have had at least one normal menstrual period (typical in duration and amount of flow for that subject) since removal of an IUD or Norplant.
  have terminated their last pregnancy at least 42 days before admission to the study.
  are not lactating.
  in good health as confirmed by the investigator after review of the subjects:
    medical history
    physical examination (including vital signs)
    gynecologic examination (including breast examination)
    laboratory test results.
  a have a sitting systolic pressure <140 mmHg and a disatolic blood pressure <90 mmHg.

are not pregnant as demonstrated by a negative serum β-subunit HCG RIA pregnancy test within 7 days prior to taking drug.

have no current evidence of cervical dysplasia.

agree to use only the assigned study drug as contraception during the study for up to 13 cycles except when back-up contraception or STD protection is required.

have read and signed the informed consent form after the nature of the study has been fully explained.

Exclusion Criteria history or presence of disorders commonly accepted as contraindications to combined oral contraceptives, including but not limited to the following:
  deep vein thrombophlebitis or thromboembolic disorders
  cerebral vascular or coronary artery disease, hypertension or severe migraines
  a benign or malignant liver tumor which developed during the use of oral contraceptives or other estrogen containing products
  known or suspected carcinoma of any body system, including the breast or genital tract
  insulin-dependent diabetes
  known or suspected estrogen-dependent neoplasia
  cholestatic jaundice.

presence of disorders commonly accepted as contraindications to oral contraceptives, including but not limited to the following:
  undiagnosed abnormal vaginal bleeding
  any neurovascular lesion of the eye or serious visual disturbance
  any impairment of liver function or liver disease, or renal disease.

are a recent (within 12 months prior to the prestudy visit) abuser of alcohol or other substances.

have received any experimental drug and/or used any experimental device within 30 days prior to the prestudy visit.

have received a DepoProvera injection (or any other depot hormone injection) within the 6 months prior to the prestudy visit.

a have used barbiturates, antiepileptics, rifampin, griseofulvin or other hepatic enzyme-inducing drugs within the 30 days prior to the prestudy visit.

uncontrolled thyroid disorder.

has been exposed to etretinate (Tegison).

concomitant use of isotretinoin (Accutane), tretinoin (Renova or RETIN-A) or has taken them within the 30 day period immediately prior to the screening visit.

deemed by the investigator to have questionable reliability in her ability to comply with the protocol and provide accurate information.

At the pre-study visit, a complete medical history with emphasis on menstrual history and use of hormonal contraceptives, was obtained for each subject. In addition, a complete physical and gynecologic examination, including vital signs, breast and pelvic exam, was conducted. A Papanicolaou (PAP) smear was done, although a smear done within 2 months with a report available prior to study entry was acceptable. An assessment of body mass index was also accomplished. At the admission visit, subjects returned in a fasted state for a hematology profile, clinical chemistries, urine dipstick and a β-subunit HCG RIA pregnancy test. Subjects randomized to the three blinded regimen groups began taking study medication on the first day of the menstrual cycle. Subjects were seen for follow-up visits at the end of cycles 1, 3, 6, 9 and 13. At each visit, vital signs were obtained and the diary cards and study drug packs were reviewed. At the cycle 6 and cycle 13 visits, blood was drawn for a hematology profile and clinical chemistries. Subjects who did not have onset of menses during the placebo tablet days of any cycle were to immediately contact the investigator and have a subunit HCG RIA performed. The following medications were not permitted during the study, as they would confound the effects of the study drug: steroid hormonal therapy, barbiturates, antiepileptics, rifampin, griseofulvin, and other hepatic enzyme inducers.

Cycle control is evaluated as the occurrence of breakthrough bleeding and/or spotting. Breakthrough bleeding and/or spotting is defined, at each cycle, as bleeding and/or spotting during the drug-administration interval that is neither continuous with drug-free bleeding or spotting of the previous cycle nor continuous without interruption into the drug-free interval.

RESULTS

The study resulted in a total of 10,990 cycles which could be used for analysis of the 25 $\mu$g EE triphasic regimen. The average body mass index of the women involved in the study was 23.7 and their average age was 28.1 years. For these study cycles, the occurrence of irregular bleeding (breakthrough bleeding and/or spotting) is shown in (Table 5). As can be seen, the incidence of irregular bleeding for this 25 $\mu$g EE triphasic regimen is unexpectedly comparable to the incidence of irregular bleeding for the 35 $\mu$g EE triphasic regimen as described in Comparative Example 1.

COMPARATIVE EXAMPLE 1

SUBJECTS AND METHODS

In an earlier and different study that that conducted in Example 1, there was conducted a randomized, multi-centered, single-cell Phase III study to evaluate a triphasic regimen of norgestimate and ethinyl estradiol (NGM/EE) oral contraceptive. In this triphasic regimen there was administered in the first phase a tablet containing 0.180 mg of norgestimate +35 $\mu$g EE once a day for 7 days; in the second phase a tablet containig 0.215 mg of norgestimate +35 $\mu$g EE once a day for 7 days; and in the third phase a tablet containing 0.250 mg of norgestimate +35 $\mu$g EE; followed by 7 days of placebo tablets. All investigators used a common protocol and case record forms. Each investigator was to enroll a block of 50 subjects for a total of 1800 subjects. Investigators were selected on the basis of their experience in family planning. Investigator sites were selected to include regions throughout the United States in clinic and private settings, in order to reduce demographic bias. Each subject was expected to complete 24 consecutive cycles of therapy and be involved in the study for a maximum of 28 months (including post-therapy follow-up).

To be admitted to the study, each woman had to meet the inclusion criteria and exhibit none of the exclusion characteristics including contraindications to oral contraceptive use.

To be eligible, women had to meet the following inclusion criteria:

1. In good health with no evidence of infertility as confirmed by medical history, physical (including vital signs) and gynecological examination
2. 18 to 38 years of age
3. not pregnant: postpartum and post-abortal subjects may be admitted to the study on their first spontaneous menses after termination of pregnancy 4. have regular menstrual cycles
5. have regular coitus
6. have a Papanicolaou smear with no evidence of dysplasia
7. agree to discontinue use of all other means of contraception during the on-therapy cycles
8. have at least one normal menstrual cycle following the removal of an intrauterine device The exclusion criteria included commonly accepted contraindications to steroid hormonal therapy, and additional study-related items as follows:

1. thrombophlebitis or thromboembolic disorders
2. a past history of deep vein thrombophlebitis or thromboembotic disorders
3. cerebral vascular or coronary artery disease
4. known or suspected carcinoma of the breast
5. known or suspected estrogen-dependent neoplasia
6. undiagnosed, abnormal genital bleeding
7. benign or malignant liver tumor which developed during the use of oral contraceptives or other estrogen-containing products
8. any neurovascular lesion of the eve or serious visual disturbance at the pre-therapy examination Also excluded were those women who had used any investigational drug within 30 days prior to admission into the study, with the exception of norgestimate.

RESULTS

The study resulted in a total of 16,718 cycles which could be used for analysis of the 35 $\mu$g EE triphasic regimen. The average weight of the women involved in the study was 135.8 pounds and their average age was 24.8. years. For these study cycles, the occurrence of irregular bleeding (breakthrough bleeding and/or spotting) is shown in (Table 5).

TABLE 5

| | Total BTB and/or Spotting (% of subjects) | |
|---|---|---|
| Cycle | 25 $\mu$g EE | 35 $\mu$g EE |
| 1 | 16.8 | 16.9 |
| 2 | 15.7 | 13.1 |
| 3 | 12.5 | 12.6 |
| 4 | 13.1 | 10.1 |
| 5 | 11.1 | 7.6 |
| 6 | 11.5 | 9.4 |
| 7–12 | 8.8 | 7.3 |

Having described the invention in specific detail and exemplified the manner in which it may be carried into practice, it will be apparent to those skilled in the art that imnumerable variations, applications, modifications, and extensions of the basic principles involved may be made without departing from its spirit or scope. It is to be understood that the foregoing is merely exemplary and the present invention is not to be limited to the specific form or arrangements of parts herein described and shown.

What is claimed is:

1. A method of contraception which comprises administering for 21 successive days to a female of childbearing age a combination of 17α-ethinylestradiol and norgestimate for the first 7 days in a daily dosage corresponding to 25 $\mu$g of 17α-ethinylestradiol and 0.180 mg of norgestimate, for the succeeding 7 days a daily dosage equal to 25 $\mu$g of 17α-ethinylestradiol aid 0.215 mg of norgestimate; and for the next 7 days a daily dosage equal to 25 $\mu$g of 17α-ethinylestradiol and 0.250 mg of norgestimate; followed by 7 days without estrogen and progestogen administration.

2. A triphasic oral contraceptive unit having 21 separate dosage units, adapted for successive daily oral administration comprising: 5–8 dosage units containing, in admixture with a pharmaceutically acceptable carrier, a combination of an estrogen and a progestogen at contraceptively effective dosages corresponding in estrogenic activity to 25 $\mu$g of 17α-ethinylestradiol and in progestogenic activity to 0.180 mg of norgestimate as a first phase; followed by 7–11 dosage units containing in admixture with a pharmaceutically acceptable carrier, a combination of an estrogen and a progestagen at a contraceptively effective dosage corresponding in estrogenic activity to 25 $\mu$g of 17α-ethinylestradiol and in progestogenic activity to 0.215 mg of norgestimate as a second phase; followed by 3–7 dosage units containing in admixture with a pharmaceutically acceptable carrier, a combination of an estrogen at a contraceptively effective dosage corresponding in estrogenic activity to 25 $\mu$g of 17α-ethinylestradiol and in progestogenic activity to 0.250 mg of norgestimate as a third phase; and optionally containing 4–8 additional dosage units free of estrogen and progestogen.

3. A method of contraception which comprises administering for 21 successive days to a female of childbearing age a combination of an estrogen and a progestogen in a contraceptively effective daily dosage in which there is a first phase of 5–8 days where the combination comprises a progestogen equivalent in effect to about 0.180 mg of norgestimate and an estrogen equivalent in effect to about 25 $\mu$g of ethinyl estradiol; followed by a second phase of 7–11 days, where the combination comprises a progestogen equivalent in effect to about 0.215 mg of a norgestimate and an estrogen equivalent in effect to about 25 $\mu$g of ethinyl estradiol; followed by a third phase of 3–7 days where the combination comprises a progestogen equivalent in effect to about 0.250 mg of norgestimate in combination with an estrogen equivalent in effect to about 25 $\mu$g of ethinyl estradiol; and followed by 4–8 days which are free of hormone administration.

4. A triphasic oral contraceptive unit having 21 separate dosage units, adapted for successive daily oral administration comprising: 7 dosage units containing in admixture with a pharmaceutically acceptable carrier, 25 $\mu$g of 17α-ethinylestradiol and 0.180 mg of norgestimate, 7 dosage units containing in admixture with a pharmaceutically acceptable carrier, 25 $\mu$g of 17α-ethinylestradiol and 0.215 mg of norgestimate; and 7 dosage units containing in admixture with a pharmaceutically acceptable carrier, 25 $\mu$g of 17α-ethinylestradiol and 0.250 mg of norgestimate; and optionally containing 7 additional dosage units free of estrogen and progestogen.

* * * * *

UNITED STATES PATENT AND TRADEMARK OFFICE
Certificate

Patent No. 6,214,815 B1                                                                Patented: April 10, 2001

On petition requesting issuance of a certificate for correction of inventorship pursuant to 35 U.S.C. 256, it has been found that the above identified patent, through error and without any deceptive intent, improperly sets forth the inventorship.

Accordingly, it is hereby certified that the correct inventorship of this patent is: David Upmalis, Newtown, PA (US).

Signed and Sealed this Fifth Day of September 2006.

SREENI PADMANABHAN
                                                                                *Supervisory Patent Examiner*
                                                                                      Art Unit 1617